United States Patent
Daniels

(10) Patent No.: US 7,214,383 B2
(45) Date of Patent: May 8, 2007

(54) STENT FOR DELIVERY OF DRUGS TO THE ENDOTHELIUM

(76) Inventor: Bruce Alan Daniels, 1721 Coventry La., Oklahoma City, OK (US) 73120

( * ) Notice: Subject to any disclaimer, the term of this patent is extended or adjusted under 35 U.S.C. 154(b) by 284 days.

(21) Appl. No.: 10/462,907

(22) Filed: Jun. 16, 2003

(65) Prior Publication Data
US 2004/0254631 A1    Dec. 16, 2004

(51) Int. Cl.
*A61F 13/00*    (2006.01)
*A61F 2/06*     (2006.01)

(52) U.S. Cl. .................... 424/422; 623/1.42

(58) Field of Classification Search ............ 424/1, 424/422–425; 623/1.39, 1.4, 1.42, 1.43, 623/1.44, 1.45, 1.46
See application file for complete search history.

(56) References Cited

U.S. PATENT DOCUMENTS

| | | | | |
|---|---|---|---|---|
| 5,500,013 | A * | 3/1996 | Buscemi et al. | 623/1.22 |
| 5,670,161 | A * | 9/1997 | Healy et al. | 623/1.42 |
| 6,071,305 | A * | 6/2000 | Brown et al. | 623/1.43 |
| 6,251,136 | B1 * | 6/2001 | Guruwaiya et al. | 623/1.46 |
| 6,641,607 | B1 * | 11/2003 | Hossainy et al. | 623/1.15 |
| 6,709,379 | B1 * | 3/2004 | Brandau et al. | 600/3 |
| 6,797,705 | B2 * | 9/2004 | Daniels | 514/54 |
| 6,805,898 | B1 * | 10/2004 | Wu et al. | 427/2.25 |
| 2004/0082807 | A1 * | 4/2004 | Meng | 560/135 |

FOREIGN PATENT DOCUMENTS

EP    0273076 A1 *    7/1988
JP    07126169 A *   11/1993

OTHER PUBLICATIONS

Deux, JF, et al. "Low molecular weight fucoidan prevents neointimal hyperplasia in rabbit iliac artery in-stent restenosis model," *Arterioscler Thromb Vasc Biol* Oct. 1 2002 vol. 22, No. 10 pp. 1604-1609.
Trento, Fabio, et al. "Antithrombin Activity of an Algal Polysaccharide" *Thrombosis Research* vol. 102, 2001 pp. 457-465.
Thierry, Benjamin, et al. "Nanocoatings onto Arteries via Layer by Layer Deposition: Toward the in VIvo repair of Damaged Blood Vessels" *J. Am. Chem. Soc.* 2003, vol. 125, No. 25, pp. 7494-7495.

* cited by examiner

*Primary Examiner*—Sharon E. Kennedy
(74) *Attorney, Agent, or Firm*—Ali Kamarei, Esq.; Alexander Chen, Esq.

(57) ABSTRACT

The present invention provides for a stent for treatment and prevention of arterial stenosis and re-stenosis. The stent for intraluminal placement within an artery and subsequent expansion for implantation in a patient comprises of a main body portion having a first end and a second end, for defining a passage for flow of blood there-through, the main body portion having an inner lumen surface and an outer lumen surface, the outer lumen surface coming into contact with the endothelium and delivering a drug composition on the outer lumen surface directly only to the endothelium for providing cell surface antithrombotic activity, wherein the anticoagulation activity in the blood plasma of a patient is not appreciably increased.

11 Claims, 4 Drawing Sheets

Rham = Rhamnose residue

S = Sulfate Ester

STENT FOR DELIVERY OF DRUGS TO THE ENDOTHELIUM

FIELD

This invention relates generally to an implantable device for the sustained delivery of a medicament and, more particularly, to a stent and method for preventing restenosis following angioplasty or atheroectomy.

REFERENCE TO RELATED PATENT APPLICATION

Reference is made and priority is claimed to patent application Ser. No. 10/320,309 now U.S. Pat. No. 6,797,705, filed Dec. 16, 2002, entitled: "Rhamnan Sulphate Composition for treatment of Endothelial Dysfunction" by the present inventor.

BACKGROUND

This invention relates to stents for maintaining flow through arterial vasculature while serving as drug delivery vehicles. The invention has particular reference to stents comprising compounds useful for the treatment and prevention of restenosis, increase in cell surface antithrombotic activity, and reduced inflammatory responses from the body of the patient receiving the stent.

Commonly used methods of treating cardiovascular disease includes angioplasty or atherectomy. While these methods are successful in relieving the symptoms of cardiovascular disease, the procedure produces a high rate of arterial re-closure or restenosis. Various methods of preventing restenosis have been tested, however, these methods have met with varying degrees of success.

Since restenosis can begin immediately after the angioplasty or atherectomy procedure and can continue for months post procedure, it is desirable to provide a device and method capable of providing the sustained delivery of a medicating composition to inhibit restenosis and to reduce the inflammatory response and effect, including an increase in cell surface anti-thrombotic activity of the endothelium.

An acceptable method of sustained long term drug delivery employs metal stents coated with a bioabsorbable synthetic polymer that have also been used to deliver medicament. However, most such metal stents are thrombogenic and being a "foreign body" stimulates the host's inflammatory response.

Preferably, such a stent should be minimally inflammatory, non-thromboginic, biologically compatible and capable of sustained drug delivery to the endothelium and provide for increased cell surface antithrombotic effect without increasing the risk of the patient becoming a "bleeder" or to be at appreciably increased risk of hemorrhaging either due to internal or external injury.

SUMMARY

The present invention provides for a stent for treatment and prevention of arterial stenosis and re-stenosis. The stent for intraluminal placement within an artery and subsequent expansion for implantation in a patient comprises of a main body portion having a first end and a second end, for defining a passage for flow of blood there-through, the main body portion having an inner lumen surface and an outer lumen surface, the outer lumen surface coming into contact with the endothelium and delivering a drug composition on the outer lumen surface directly only to the endothelium for providing cell surface antithrombotic activity, wherein the anticoagulation activity in the blood plasma of a patient is not appreciably increased. The outer lumen of the stent is optionally coated with one or more layers of one or more drugs, preferably Rhamnan Sulphate and/or Arginine. Also as an option, Rhamnan Sulfate and Arginine are covalently bound together.

One advantage of the method and composition of the invention is that it possesses extremely potent cell surface and matrix antithrombotic activity and other effects, which lead to, increased eNOs activity and reduced free radical damage to cells.

Another advantage of the described composition is that there is less peptide residual in extracting the composition from plant cells as compared to heparin from animal cells. Hence, it is less allergic reaction prone and has fewer immunogenic properties.

Yet another advantage is that since Rhamnan Sulphate is from plant cells, it has no potential for the transmission of potentially lethal and serious prion diseases such as mad cow disease.

DETAILED DESCRIPTION

Figure 1:
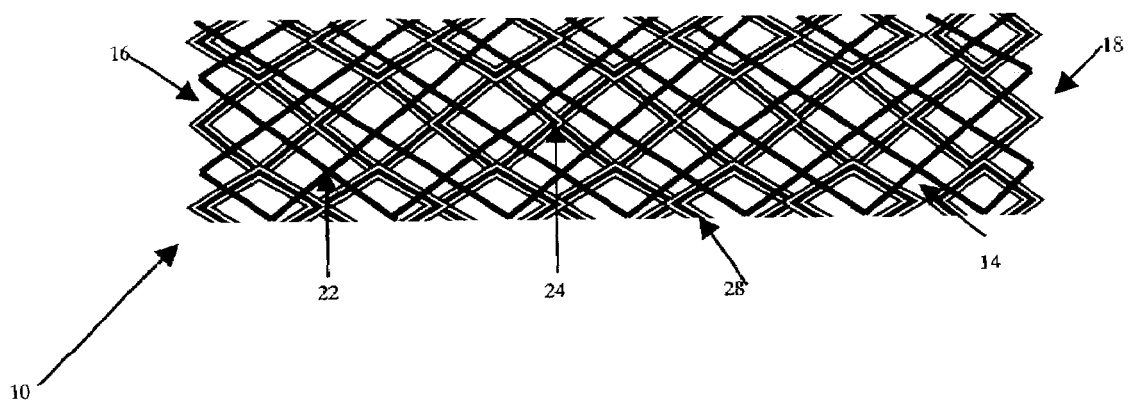
FIG. 1 is a side view of a stent with a layer of drug composition on the outer lumen of the stent for delivery of the drug composition to the endothelium.
Figure 2:
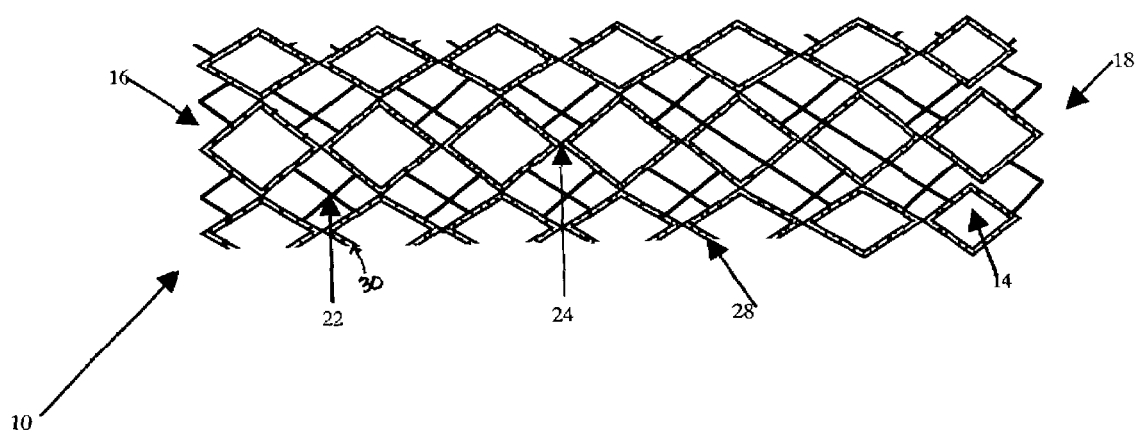
FIG. 2 is a side view of a stent with pores and reservoirs on the outer lumen of the stent containing the drug composition.
Figure 3:
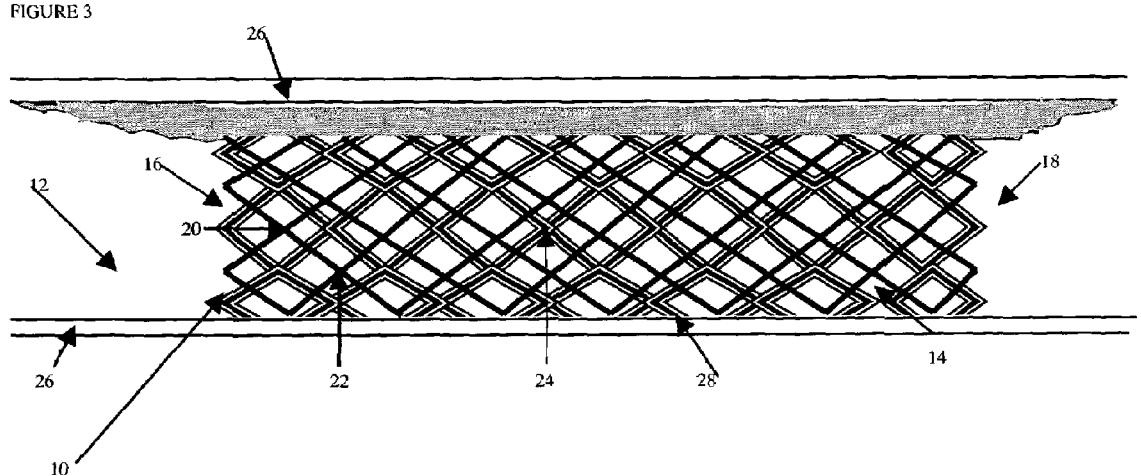
FIG. 3 shows a side view of the artery with the stent deployed in the artery adjacent to the target tissue and with the angioplasty catheter removed.

The inventor, in U.S. Pat. Nos. 6,255,296 and 6,495,530, outlines the fact that a disruption in the structure of the cellular environment, and in particular the endothelial cells, is the proximate cause of diseases such as cardiovascular disease. As has been previously described it is a conception of the inventor that a cellular environment (cellular matrix or gel matrix) composed of charged polymers-highly charged peptide-water polymers, such as heparin-arginine-water is responsible for controlling the structure and ultimately the function of human cells within this cellular environment.

This charged polymer-arginine-water environment impacts such important functions of the cells by effecting protein distribution and functionality, cell signaling processes, genetic or DNA-RNA transcription regulation, and the physical/chemical properties of cells, including blood vessel wall cells. The specifications of those patents are hereby incorporated by reference herein.

While not bound to a particular mechanism of operation, the inventor's conception is that the loss of heparin sulfate causes a reduction in Nitric Oxide formation. Moreover, there is a synergistic (positive feedback) effect between increased concentrations of heparin sulfate and increased Nitric Oxide ("NO") production. Meaning that increased NO production aids in the production of heparin sulfate and increased heparin sulfate induces increased NO production. Endothelial-derived Nitric Oxide (EDNO) is recognized to decrease inflammation through down regulation of NF kappa B, and to decrease INOS activity accompanying endothelial and vascular cell inflammation. Additionally, it is recognized that EDNO decreases the endothelial expression of various mediators of inflammatory cell recruitment and adhesion through decreased selection and macrophage chemotaxis factor. EDNO also reduces platelet activation and adhesion processes attendant to endothelial injury and plaque rupture, thereby, it reduces cell surface clotting activity.

In its parent application, applicant has described a novel composition, which is used for treatment of endothelial dysfunction and more particularly cardiovascular disease. This composition is also effective in reducing inflammation in areas of endothelial and arterial cell injury or abnormal physiologic function due to its ability to increase heparin sulfate production and NO production.

The present invention is directed to delivery of a composition comprising of an exogenous heparan directly to the endothelium without delivery of the composition into the blood plasma after installing the stent in the desired location.

The composition comprises of Rhamnan Sulfate. Rhamnan Sulfate is derived from dried green Algae (Monostroma Nitidum) that were swollen in 10 Vols. of water at room temperature for one hour. Thereafter the swollen green algae was ground and refluxed for two (2) hours in a boiling water bath. The water extract was centrifuged (4500 g) for 30 minutes, and the water-soluble polysaccharide in the non-dialyzable fraction was obtained by lyophilization.

The crude polysaccharide was dissolved in water and was applied to a column (2.4×100 cm) of DEAE-cellulose (Whatman DE-52). Starch or neutral polysaccharides were removed by continuous water elution until the sample was completely free as determined by phenol-sulfuric acid detection. Afterwards, acid polysaccharide was fractionated by stepwise alteration of the ionic strength of KCL at 0.5. 0.7 and 2.0 M, and then each fraction were desalted and freeze dried. The 0.5 M KCL fraction (major fraction) successive purification procedures were performed by gel filtration chromatography on a Toyopearl HW-65 (fine) column (1.2× 100 cm). The sample was eluted with water at a flow rate of 0.4 ml/min. The major fraction was collected and freeze dried. These procedures or variations of them for extraction of Rhamnan Sulphate is well known.

Rhamnan Sulphate was prepared as described above and was tested for cell surface anti-thrombotic activity, as described below. Rhamnan sulphate was dissolved in water at concentrations 20, 10 and 5 mg/ml. For experiments utilizing L-Arginine, L-Arginine capsules were opened and contents were dissolved in water at 300 mg/ml for 4 hr studies and 150 mg/ml for the 28 day study. Rhamnan sulphate-arginine complex (RS-LR), where L-Arginine is covalently bound to Rhamnan Sulphate to form a physiologically acceptable salt of Rhamnan Sulphate, was dissolved in water at concentrations of 20, 10, 3 and 0.3 mg/ml. Bovine ung unfractionated heparin,150 units/mg, Lot No ZX320, was obtained from Upjohn Ltd. Heparin was dissolved in water at a concentration of 20 mg/ml.

One hundred and two male Wistar rats, weighing 312±64 g (±SD), were handled and housed according to the Principles of Animal Care set out by the Canadian Federation of Biological Societies. The animals were fasted overnight prior to treatment and were anesthetized with barbital and methoxyflurane for experimental procedures.

Rhamnan sulphate was administered to rats at 7.5, 4 and 2 mg/kg with 5, 20, and 5 rats/group respectively. Rhamnan sulphate (7.5 mg/kg) plus arginine (112.5 mg/kg) was administered to 5 rats. Rhamnan sulphate-arginine complex was administered to rats at 4, 1 and 0.1 mg/kg with 20 rats/group. The rhamnan-arginine complex was weighed fresh daily. All of the Groups and the administered compounds are shown in Table 1. Six to 8 rats were treated per day. A stomach tube was filled with 0.2 ml saline followed by 0.09–0.18 ml of the rhamnan sulphate solutions or 0.1 ml of arginine solution depending on rat weight. Thus when the stomach tube was placed in the stomach the drugs were first introduced into the stomach followed by saline to give a total volume of approximately 0.4 ml. In the heparin alone group, heparin was administered in a volume of 0.1–0.2 ml followed by 0.2 ml saline. Control group was saline alone.

TABLE 1

| Group 1 | No Treatment |
|---|---|
| Group 2 | Heparin alone at 7.5 mg/kg |
| Group 3 | Rhamnan Sulphate alone at 7.5 mg/kg |
| Group 4 | Rhamnan Sulphate alone at 4 mg/kg |
| Group 5 | Rhamnan Sulphate alone at 2 mg/kg |
| Group 6 | Rhamnan Sulphate 7.5 mg/kg + L-Arginine 112 mg/Kg |
| Group 7 | Salt of Rhamnan Sulphate 4 mg/kg – L-Arginine |
| Group 8 | Salt of Rhamnan Sulphate 1 mg/kg – L-Arginine |
| Group 9 | Salt of Rhamnan Sulphate 0.1 mg/kg – L-Arginine |

Thrombosis Test

The thrombosis test was performed by a modification of the procedure by Blake et al. For animals exposed to treatment for 4 h, a thrombus was initiated in the right jugular vein by application of 10% formalin in 65% methanol to the exposed adventitial surface. Immediately following, drugs were introduced into the stomach by stomach tube. At 4 h after thrombus initiation animals were again deeply anesthetized and first examined for any external signs of bleeding. The jugular vein was exposed and examined for the presence of a plug using a cotton pledget. The clot was scored as+ (hard clot) if the vessel is blocked and remained blocked despite examination with a cotton pledget. The clot was scored as+/– (soft clot) if the vessel appeared completely blocked on first examination and then opened as it was examined. The thrombus was scored as – (negative) if blood was seen to flow freely in the vessel.

Collection of Blood and Blood Vessels.

Immediately after examination of the jugular vein, a laparotomy was performed and a blood sample of approximately 10 ml (9 parts blood to 1 part 3.8% sodium citrate) was taken from the abdominal aorta. Plasma was prepared. As a source of endothelium, the thoracic aorta or vena cava was removed and placed in saline. Each animal was examined for signs of internal hemorrhage and the time when blood clotted in the body cavity was recorded.

Harvesting of Endothelium

Endothelium was removed from blood vessels according to the method of Hiebert and Jaques. The vessels were slit open, pinned to dental wax lumen side up, and rinsed in Locke's solution. Cellulose acetate paper was applied to the lumenal surface and when lifted, endothelium was removed. The length and width of the imprint were measured to the nearest mm.

Determination of Heparin-Like Compounds with Endothelium

Cellulose acetate paper was removed from endothelium by dissolving in cold acetone followed by centrifuging and discarding the supernatant. The precipitates were further processed by digestion with pronase (10 μl of 40 mg/ml in Tris buffer). Samples were then centrifuged at 10,000 rpm for 10 min, supernatant was collected and the precipitate washed twice with 100 μL 26.8% NaCl which was added to the supernatant. GAGs were precipitated from the supernatant with five volumes of methanol and the precipitate dried. Agarose gel electrophoresis was used to identify and measure rhamnan sulphate in endothelial extracts by previously published methods. The dried powders, dissolved in suitable volumes of water, were applied to agarose gel slides along with the administered rhamnan sulphate used as a reference. Following electrophoresis, gels were fixed in 0.1% hexadecyltrimethylammonium bromide and air-dried. Slides were stained with 0.04% toluidine blue in 80% acetone and background color was removed with 1% acetic acid. Heparin was identified by electrophoretic migration as compared to reference material and amounts determined by densitometry.

Statistical Analysis

Thrombosis data is expressed as a percentage with 95% confidence intervals. $X^2$ test for differences between proportions was used to compare the total thrombotic incidence and incidence of hard clots between groups. Other data is expressed as mean ±SE. A one-way ANOVA with Tukeys post hoc test was used to compare the differences between groups when plasma coagulation tests and heparin-like concentrations in urine were examined.

Thrombosis Test

Antithrombotic effect was observed with all oral doses of rhamnan sulphate alone, except 2 mg/kg. As well an antithrombotic effect was seen when arginine was added along with rhamnan sulphate or when rhamnan sulphate was complexed to arginine. At 2 mg/kg rhamnan sulphate there was a trend towards a significant reduction in hard clots versus controls although this did not reach significance. A dose response was evident with both rhamnan sulphate alone or when rhamnan sulphate was complexed to arginine. The rhamnan sulphate arginine complex was a significantly more effective antithrombotic agent than rhamnan sulphate alone as shown by a decrease in incidence of hard clots when comparing the compounds at 4 mg/kg. Further the incidence of hard clots and total thrombotic incidence was less for the rhamnan sulphate arginine complex at 1 mg/kg versus rhamnan sulphate alone at 2 mg/kg.

Antithrombotic activity of orally administered rhamnan sulphate or rhamnan sulphate and arginine as compared to oral unfractionated heparin was shown.

Plasma Levels

The Rhamnan Sulphate Groups at all doses did not have a significant effect on APTT or the Heptest (Table 2). Rhamnan sulphate alone or when complexed with arginine had little or no effect on anti-Xa or anti-IIa activity. Rhamnan sulphate alone had somewhat more anti-Xa activity than the rhamnan sulphate-arginine complex. When anti-Xa activity was measured in the plasma of rats there was a reduced optical density in the plasma samples from some of the rats given rhamnan sulphate or the rhamnan sulphate-arginine complex. (Data not shown). There was no evidence of bleeding or blood loss in the animals.

TABLE 2

Activation partial thromboplastin time and Heptest following oral administration of rhamnan sulphate alone, with arginine or as a rhamnan sulphate-arginine complex.

|  | Dose Mg/kg | APTT (sec) Mean | APTT (sec) SE | Heptest (sec) Mean | Heptest (sec) SE |
|---|---|---|---|---|---|
| Rhamnan Sulphate | Controls | 19.5 | 0.9 | 36.3 | 0.8 |
|  | 7.5 | 20.2 | 0.6 | 32.5 | 2.2 |
|  | 4 | 20.5 | 0.5 | 34.2 | 1.9 |
|  | 2 | 21.8 | 0.9 | 36.5 | 1.1 |
| Rhamnan sulphate + LR | 7.5 | 20.4 | 0.8 | 31.8 | 0.9 |
| Rhamnan Sulphate-Arginine Complex | 4 | 22.6 | 1.5 | 36.9 | 1.0 |
|  | 1 | 18.5 | 0.7 | 30.8 | 0.7 |
|  | 0.1 | 18.5 | 0.7 | 30.8 | 1.0 |

Rhamnan sulphate like material was also found on both aortic and vena caval endothelium. A higher concentration was found on the vena cava than on the aorta when all compounds were administered (Table 3) P<0.00003 one-tailed t-test. A dose effect was evident when venal caval concentrations of rhamnan sulphate were observed following rhamnan sulphate or rhamnan sulphate-arginine. A similar dose effect was seen for aortic concentrations of rhamnan sulphate following oral administration of rhamnan sulphate arginine but not rhamnan sulphate alone. Venal caval but not aortic concentrations were greater at 4 mg/kg for rhamnan but not rhamnan sulphate-arginine complex.

TABLE 3

Rhamnan sulphate - like material found on aortic and vena caval endothelium following oral administration of rhamnan sulphate alone, with arginine or as a rhamnan sulphate-arginine complex.

|  | Dose Mg/kg | Number | Aorta μg/cm$^2$ mean ± se | Vena Cava μg/cm$^2$ mean ± se |
|---|---|---|---|---|
| Rhamnan Sulphate | 7.5 | 5 | 1.80 ± 0.79 | 11.22 ± 3.20 |
|  | 4 | 20 | 2.05 ± 0.08 | 15.97 ± 1.54* |
|  | 2 | 5 | 2.32 ± 0.33 | 3.00 ± 0.43 |
| Rhamnan sulphate ± LR | 7.5 | 5 | 3.91 ± 0.65 | 7.16 ± 3.77 |
| Rhamnan Sulphate-Arginine Complex | 4 | 20 | 2.30 ± 0.07 | 4.41 ± 0.05 |
|  | 1 | 20 | 0.12 ± 0.05 | 0.42 ± 0.10 |
|  | 0.1 | 20 | 0.52 ± 0.13 | 1.89 ± 0.43 |

Rhamnan sulphate was found in urine following oral administration. Mean±SEM is shown. Rhamnan sulphate-like material was also recovered from the urine and feces accumulated over the 4 hr period. The amounts and concentrations recovered after administration of rhamnan sulphate alone resulted in more being excreted in the urine than when given as a rhamnan sulphate-arginine complex. Amounts recovered were 3.0±0.4 and 1.6±0.4 (mean±SE) percent of dose for rhamnan sulphate alone versus rhamnan sulphate-arginine respectively and was significantly greater at 4mg/kg, in a one tailed t-test.

The amounts recovered from feces show that more is recovered when administered as rhamnan sulphate alone versus rhamnan sulphate-arginine. A dose effect was evident. Amounts recovered were 13.7±4.4 and 6.1±1.9 (mean±SE) percent of dose for rhamnan sulphate alone versus rhamnan sulphate-arginine respectively, these differences were not significant.

In general, the results indicate that Rhamnan Sulphate provides vessel surface anti-thrombotic activity without appreciably increasing plasma anticoagulation activity. Hard clots and soft clots build from the inside surface of the lumen of the injured vessel and extend radially more central into the lumen of the vessel, but there is little or no change in the plasma coagulation activity as was measured by the standard plasma coagulation tests mentioned above. Thus, Rhamnan Sulphate is effective in preventing clot formation at the inside surface of the vessel, but it does not provide the patient with increased plasma anti-coagulation activity to render the patient a "bleeder" or to be at appreciably increased risk of hemorrhaging.

The results show that without any treatment, as a control group, saline had no effect on thrombosis with approximately a 90% incidence of thrombosis of which a very high percentage were hard clots. Heparin, which is commonly used as an anticoagulant, at 7.5 mg/kg showed little or no effect in total incidence of thrombosis, however it reduced the percentage of incidence of hard clots. Conversely, Rhamnan Sulphate at the same 7.5 mg/kg dosage showed a significant decrease in incidence of thrombosis with little or no hard clots. Reduction of the dosage of Rhamnan Sulphate to 4 mg/kg and 2 mg/kg resulted in the increase in incidence of thrombosis and in the re-appearance of hard clots from the 7.5 mg/kg dose.

Figure 4:
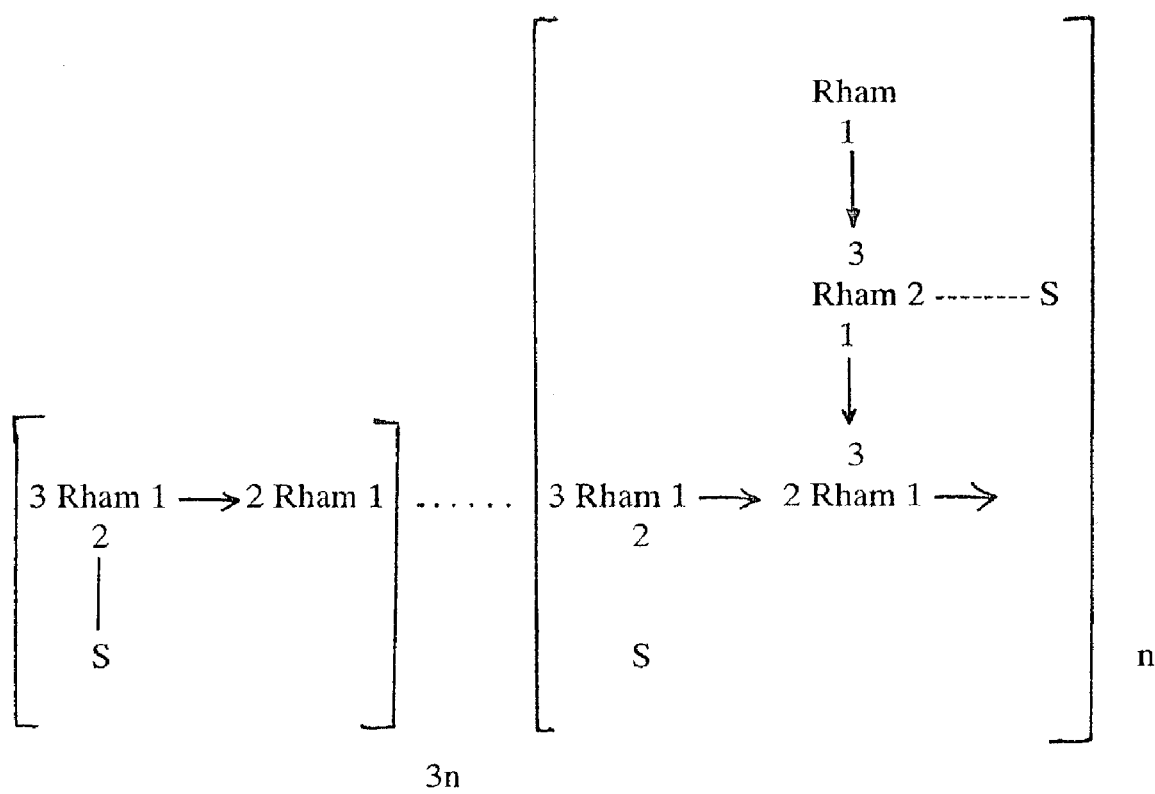
FIG. 4 shows the chemical structure of Rhamnan Sulphate.

The control group was also compared to the co-administration of Rhamnan Sulphate with L-Arginine, the structure of which is commonly known. RS+LR refers to the co-administration of Rhamnan Sulphate, whereas RS–LR refers to the salt of Rhamnan Sulphate with arginine as a compound, the chemical structure of which is shown in FIG. 4. Group 6, RS+LR at 7.5 mg/kg, showed little difference with administration of Rhamnan Sulphate by itself both in the incidence of thrombosis and in the non-occurring of hard clots. Group 7, RS–LR compound at 4 mg/kg, however, showed a significant reduction in the total incidence of thrombosis from 4 mg/kg of Rhamnan Sulphate alone and a reduction in hard clots. Even Group 8, LS–LR compound at 1 mg/kg showed a slight decrease in incidence of thrombosis than and hard clots than 4 mg/kg of Rhamnan Sulphate.

The result is that Rhamnan Sulphate by itself is more effective than Heparin in lowering the incidence of thrombosis and in reducing the number of hard clots. Further, that the blood anticoagulation activity is not appreciably increased. This further desired effect is opposite that of Heparin, which is known to increase plasma anticoagulation activity. Thus, the use of Rhamnan Sulphate in treatment of endothelial dysfunction, particularly cardiovascular disease, and more particularly atheresclerosis and arteriosclerosis is desired. A second result is that the salt of Rhamnan Sulphate-arginine compound is more effective in lowering the incidence of thrombosis and hard clots than an equivalent dose of Rhamnan Sulphate alone.

Method of Using the Endothelium Drug Delivery Stent

The stent device of the invention and an exemplary method for using the stent is shown in FIG. 1. The stent 10 is designed for intraluminal placement within an artery 12 and subsequent expansion for implantation in a patient. The main body portion 14 having a first end 16 and a second end 18, for defining a passage for flow of blood therethrough 20. The main body portion 14 also having an inner lumen surface 22 and an outer lumen surface 24, only the outer lumen surface coming into contact with the endothelium 26. In one embodiment, the outer lumen surface 24 being coated with a drug composition 28 which comes into contact with the endothelium 26. As used in this application, the term "drug" or "drug composition" denotes any compound which has a desired pharmacologic effect of cell surface antithrombotic activity or increased eNOs activity, or decreases inflammatory response and effects by the host or patient body.

The drug composition is optimally selected for providing cell surface antithrombotic activity, wherein the anticoagulation activity in the blood plasma of a patient is not appreciably increased. For example, such cell surface antithrombotic drug composition is Rhamnan Sulphate which also increases NO production. In another embodiment, the stent 10 has an outer lumen surface 24 coated with a second layer of another drug composition, such as a drug composition that increases the level of eNOs production in the endothelium. For example, such drug composition for increasing the level eNOs production in the endothelium is selected from the group of Arginine and polyarginine. In an alternative preferred embodiment, a first layer of a drug composition is the combination of Rhamnan Sulphate and Arginine or polyarginine. In an embodiment, the Rhamnan Sulfate and arginine or polyarginine are covalently bound together. In another embodiment, a drug composition comprised of one or more drugs may be loaded into reservoirs with pores 30 located on the outer lumen surface 24. It is understood that other methods of producing a stent for delivery of the desired cell surface antithrombotic effect may be used to deliver a desired drug composition directly to the endothelium.

Rhamnan Sulfate is preferably extracted from algae, selected from the group comprising of Monostroma Nitidum and Monostroma Latissimum, the method of which is known in the art. The dose of Rhamnan Sulphate delivered to the endothelium is preferably equivalent to between approximately 5,000 IU and 20,000 IU of heparin activity on a daily basis. A more preferred dose of Rhamnan Sulphate delivered to the endothelium is equivalent to between approximately 8,000 IU and 12,000 IU of heparin activity on a daily basis. It is understood that Rhamnan Sulphate is substituted for by its functional analogs at various dosages to achieve the desired effect of cell surface antithrombotic activity. Arginine or polyarginine may also be substituted by its functional analog at various doses in order to achieve increases eNOs activity or reduced inflammatory effects in the endothelium.

Example of Using the Stent for Preventing Restehosis Following Atherectomy or Angioplasty The above described stent 10, coated with the desired drug composition is implanted within the desired arterial vasculature. To deploy the stent, standard angioplasty procedures are used to deliver the stent through the femoral artery or other arterial point of entry. In summary, following identification of the target tissue comprising atheromatous plaque on the wall of the vessel, the stent should be deployed in the area of injury.

Stents to which the present invention relates may be either balloon expandable or self-expanding as well as springy in form. For example, self-expanding stents are known which are braided, woven or mesh-like in structure, although many other types of self-expanding stents including solid stents are also known.

The invention has been described in connection with what is presently considered to be the most practical and preferred embodiments. However, the above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A stent for intraluminal placement within an artery and subseciuent exvansion for implantation in a patient, comprising;
   a. a main body oortion having a first end and a second end, for defining a passage for flow of blood there-through,
   b. the main body nortion having an inner lumen surface and an outer lumen surface, the outer lumen surface coming into contact with the endothelium and delivering a drug composition on the outer lumen surface directly only to the endothelium for providing cell surface antithrombotics activity, and the inner lumen surface free of the drug composition, wherein the anticoagulation activity in the blood plasma of a patient is not appreciably increased, and wherein the outer lumen of the stent is coated with one or more layers of one or more drugs, and wherein a drug layer is comprised of Rhamnan Sulnhate.

2. The stent of claim 1, wherein the drug layers are comprised of Rhanman Sulfate and Arginine.

3. The stein of claim 2, wherein the Rhamnan Sulfate and Arginine are covalently bound together.

4. The stent of claim 1 wherein the Rhamnan Sulphate is extracted from algae.

5. The stern of claim 4 wherein the algae is selected from the group comprising of Monostroma Indiums and Monostroma Latissimum.

6. The stent of claim 1 wherein the dose of Rhamnan Sulphate is equivalent to between approximately 5,000 IU and 20,000 IU of heparin activity on a daily basis.

7. The stent of claim 1 wherein the dose of Rhainnan Sulphate is equivalent to between approximately 8,000 IU and 12,000 IU of heparin activity on a daily basis.

8. A stent for intraluminal placement within an artery and subsequent expansion for implantation in a patient, comprising;
   a. a main body portion having a first end and a second end, for defining a passage for flow of blood there-through,
   b. the main body portion having an inner lumen surface and an outer lumen surface, the outer lumen surface coming into contact with the endothelium and delivering a drug composition on the outer lumen surface directly only to the endothelium for providing cell surface antithrombotics activity, and the inner lumen surface free of drug composition, wherein the anticoagulation activity in the blood plasma of a patient is not appreciably increased, and wherein the outer lumen of the stent is coated with one or more layers of one or more drugs, comprising of Rhamnan Sulphate.

9. The stent of claim 8, wherein the drug layers are comprised of Rhamnan Sulfate and Arginine.

10. The stent of claim 9, wherein the Rhamnan Sulfate and Arginine are covalently bound together.

11. A stent for intraluminal placement within an artery and subsequent expansion for implantation in a patient, comprising; a. a main body portion having a first end and a second end, for defining a passage for flow of blood therethrough, the main body portion having an inner lumen surface and an outer lumen surface, the outer lumen surface coming into contact with the endothelium and delivering a drug composition on the outer lumen surface directly only to the endothelium for providing cell surface antithrombotic activity, wherein the outer lumen of the stent is coated with one or more layers of the drug composition comprising of Rhamnan Sulphate and Arginine.

* * * * *